United States Patent [19]
Hansenne

[11] Patent Number: 6,024,944
[45] Date of Patent: Feb. 15, 2000

[54] ANTISAN COMPOSITION CONTAINING A SOLID ELASTOMERIC ORGANOPOLYSILOXANE

[75] Inventor: Isabelle Hansenne, Paris, France

[73] Assignee: Societe L'Oreal S.A., Paris, France

[21] Appl. No.: 09/171,433

[22] PCT Filed: Feb. 3, 1998

[86] PCT No.: PCT/FR98/00191

§ 371 Date: Jan. 28, 1999

§ 102(e) Date: Jan. 28, 1999

[87] PCT Pub. No.: WO98/35649

PCT Pub. Date: Aug. 20, 1998

[30] Foreign Application Priority Data

Feb. 17, 1997 [FR] France ................... 97 01811

[51] Int. Cl.[7] .............. A61K 7/42; A61K 7/44; A61K 7/00; A61K 31/74
[52] U.S. Cl. .......... 424/59; 424/60; 424/78.02; 424/78.03; 424/400; 424/401; 514/937; 514/938; 514/943
[58] Field of Search ............... 424/59, 60, 400, 424/401, 78.02, 78.03; 514/937, 938, 943

[56] References Cited

U.S. PATENT DOCUMENTS 5,266,321  11/1993  Shukuzaki et al. ............. 424/401

FOREIGN PATENT DOCUMENTS 0 295 886  12/1988  European Pat. Off. .
0 610 026  10/1994  European Pat. Off. .
2 509 989   1/1983  France .

OTHER PUBLICATIONS

Chemical Abstracts, vol. 126, No. 8, Feb. 24, 1997, Columbus, Ohio, Abstract No. 108664, Kuroda, Akihiro et al, "Sunscreens containing metal oxides, polyoxyalkylene–polysiloxanes, and elastomers or resin waxes" XP002047963.

Chemical Abstracts, vol. 126, No. 3, Jan. 20, 1997, Columbus, Ohio, Abstract No. 36869, Aizawa, Masanori et al, "Cosmetics containing organopolysiloxane elastomers and UV absorbents for prevention of sunburn" XP002047964.

*Primary Examiner*—Shelley A. Dodson
*Attorney, Agent, or Firm*—Burns, Doane, Swecker & Mathis, L.L.P.

[57] ABSTRACT

The invention relates to an antisun composition with a high degree of protection, containing water-soluble and liposoluble screening agents, combined with a solid elastomeric organopolysiloxane, which has noteworthy cosmetic properties. It is in the form of a water-in-oil or oil-in-water emulsion. The invention also relates to a process for protecting the skin or the lips against solar radiation, containing this composition.

16 Claims, No Drawings

ANTISAN COMPOSITION CONTAINING A SOLID ELASTOMERIC ORGANOPOLYSILOXANE

The invention relates to an antisun composition of emulsion type containing a solid elastomeric organopolysiloxane, having a high degree of protection against solar radiation. The invention also relates to a process for protecting the skin and/or the lips against solar radiation, which consists in applying this composition to the skin and/or the lips.

With the ever-increasing knowledge of the damage caused by solar rays (either natural or artificial) on the skin and the excessive behaviour of human beings who always desire to have a "good complexion", cosmeticians are seeking to manufacture antisun compositions of increasingly high performance, as regards the antisun protection and the remanence or resistance to water of these compositions. This remanence in particular allows human beings to bathe after they have been covered with antisun product, while at the same time being effectively protected against solar rays.

In order to obtain a composition with a high degree of protection, generally represented by the SPF (sun protection factor), emulsions are especially used, in particular oil-in-water emulsions, containing one or more hydrophilic or water-soluble screening agents combined with [lacuna] or more specific lipophilic or liposoluble screening agents in the name of the Applicant. According to this technique, the improvements in the SPF obtained are based on the synergistic combination of specific hydrophilic and lipophilic screening agents (such as benzene-1,4-di (3-methylidene-10-camphorsulphonic acid) and 2-ethylhexyl α-cyano-β,β-diphenylacrylate (which is the case of Application EP-A-0,685,228)) in standard oil-in-water emulsions, such that these improvements cannot be obtained generally, i.e. irrespective of the hydrophilic and lipophilic screening agents used.

Lipophilic screening agents have the advantage of giving the composition good properties of remanence to water. Thus, the higher the concentration of lipophilic screening agents, the greater the properties of remanence to water and screening power. However, the use of these lipophilic screening agents at high concentration has the drawback of giving the composition a greasy and shiny appearance, which is often considered as a drawback, in particular by individuals with greasy skin.

Thus, the need remains for an antisun composition comprising both hydrophilic screening agents and lipophilic screening agents and whose SPF is high and stable over time, irrespective of the hydrophilic and/or lipophilic screening agents used, while at the same time having a non-greasy appearance.

The composition of the invention applies both to the skin and to the lips. It can be in the form of a care or treatment cream, as well as in the form of a make-up product.

More precisely, the subject of the invention is an antisun composition comprising an aqueous phase containing at least one water-soluble screening agent, a fatty phase containing at least one liposoluble screening agent and at least one partially crosslinked, elastomeric, solid organopolysiloxane which serves as gelling agent.

The term "elastomeric" is understood to refer to a flexible, deformable material which has viscoelastic properties and in particular has the consistency of a sponge or of a flexible sphere.

The elastomeric organopolysiloxanes of the composition according to the invention have remarkable oil-gelling power. They do not dry out the skin and they provide good cosmetic properties. These novel elastomers lead to compositions which are comfortable when applied and feel soft, non-greasy and non-sticky. This softness is due in particular to the texture of organopolysiloxanes.

The composition of the invention can be in the form of a paste or a cream. It can be an oil-in-water or water-in-oil emulsion.

The elastomeric organopolysiloxanes of the composition according to the invention are generally partially or totally crosslinked and of three-dimensional structure. When included in a fatty phase, they become converted, depending on the content of fatty phase used, from a product of spongy appearance when they are used in the presence of low contents of fatty phase, into a more or less homogeneous gel in the presence of larger amounts of fatty phase. The gelation of the fatty phase by these elastomers can be total or partial.

The elastomers of the composition of the invention are vehicles generally in the form of a gel consisting of an elastomeric organopolysiloxane of three-dimensional structure, included in at least one hydrocarbon-based oil and/or a silicone oil and/or a fluoro oil.

The elastomeric organopolysiloxanes of the composition according to the invention can be chosen from the crosslinked polymers described in Application EP-A-0,295,886. According to that Application, they are obtained by addition reaction and crosslinking, in the presence of a platinum-type catalyst, of at least:

(a) an organopolysiloxane having at least two lower alkenyl groups per molecule; and (b) an organopolysiloxane having at least two hydrogen atoms linked to one silicon atom per molecule.

The elastomeric organopolysiloxanes of the composition according to the invention can also be chosen from those described in U.S. Pat. No. 5,266,321. According to that patent, they are chosen in particular from:

i) organopolysiloxanes comprising units $R_2SiO$ and $RSiO_{1.5}$ and optionally units $R_3SiO_{0.5}$ and/or $SiO_2$ in which the radicals R, independently of each other, represent a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1/1 to 30/1;

ii) organopolysiloxanes which are insoluble and swellable in a silicone oil, obtained by addition of an organohydrogenopolysiloxane (1) and an organopolysiloxane (2) having unsaturated aliphatic groups such that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic.

The organopolysiloxanes which are the subject of the invention are, for example, those sold under the names KSG6 from Shin-Etsu, Trefil E-505C or Trefil E-506C from Dow-Corning, Gransil from Grant Industries (SR-CYC, SR DMF10, SR-DC556), or those sold in the form of preconstituted gels (KSG15, KSG17, KSG16, KSG18 from Shin-Etsu, Gransil SR 5CYC gel, Gransil SR DMF 10 gel, Gransil SR DC 556 gel, SF 1204 and JK 113 from General Electric). A mixture of these commercial products can also be used.

Preferably, the organopolysiloxane(s) is (are) present, as active material, at a concentration ranging from 0.1 to 80% of the total weight of the composition, and preferably from 0.5 to 60%.

The antisun cosmetic compositions according to the invention can contain one or more UVA-active and/or UVB-active hydrophilic sunscreens (absorbers), combined with one or more UVA-active and/or UVB-active lipophilic sunscreens. These complementary screening agents can be chosen in particular from cinnamic derivatives, salicylic derivatives (lipophilic screening agents), camphor derivatives, benzimidazole sulphonic derivatives, triazine derivatives (lipophilic screening agents), benzophenone derivatives, dibenzoylmethane derivatives, β, β-diphenylacrylate derivatives, p-aminobenzoic acid derivatives (hydrophilic screening agents), and lipophilic screening silicones and screening polymers, described in Application WO-93/04665.

a) Hydrophilic Screening Agents

As hydrophilic screening agents which can be used in the invention, mention may be made of those described in Application EP-A-678,292. These hydrophilic screening agents are those containing at least one carboxylic or better still sulphonic acid radical. This acid radical can be in free form or in partially or totally neutralized form. According to the invention, it is, needless to say, possible to use one or more hydrophilic screening agents containing acid functionality.

As examples of acidic screening agents containing at least one $SO_3H$ group, mention may be made more particularly of 3-benzylidine-2-camphorsulphonic derivatives and in particular those of formulae (1), (II), (III), (IV) and (V) below:

Formula (I)

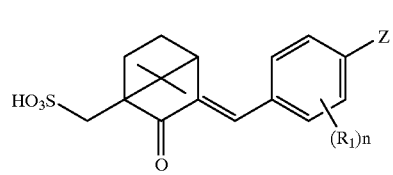

in which:

Z denotes a group:

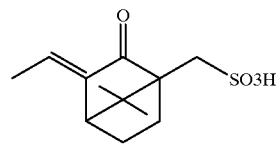

n is equal to 0 or is an integer between 1 and 4 ($0 \leq n \leq 4$), $R_1$ represents one or more identical or different, linear or branched alkyl or alkoxy radicals containing from 1 to 4 carbon atoms approximately.

A particularly preferred compound of formula (I) is the one corresponding to n=0, i.e. benzene-1,4-[di(3-methylidenecamphor-10-sulphonic acid)].

This screening agent is a broad-band screening agent capable of absorbing ultraviolet rays with wavelengths of between 280 nm and 400 nm, with absorption maxima of between 320 nm and 400 nm, in particular at about 345 nm. It is used in acid form or salified with a base chosen from triethanolamine, sodium hydroxide and potassium hydroxide. In addition, it can be in cis or trans form. This screening agent is known under the trade name Mexoryl SX.

Formula (II)

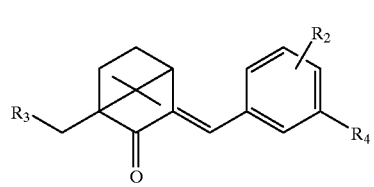

in which;

$R_2$ denotes a hydrogen atom, a halogen atom, an alkyl radical containing from 1 to 4 carbon atoms approximately or an $—SO_3H$ radical, $R_3$ and $R_4$ denote a hydrogen atom or an $—SO_3H$ radical, at least one of the radicals $R_2$, $R_3$ or $R_4$ denoting the $—SO_3H$ radical, it not being possible for $R_2$ and $R_4$ simultaneously to denote an $—SO_3H$ radical.

As specific examples, mention may be made of the following compounds of formula (II) in which:

$R_2$ denotes the $—SO_3H$ radical in the para position of the benzylidenecamphor and $R_3$ and $R_4$ each denote a hydrogen atom, i.e. 4-(3-methylidenecamphor) benzenesulphonic acid.

$R_2$ and $R_4$ each denote a hydrogen atom and $R_3$ denotes an $—SO_3H$ radical, i.e. 3-benzylidenecamphor-10-sulphonic acid.

$R_2$ denotes a methyl radical in the para position of the benzylidenecamphor, $R_4$ denotes an $—SO_3H$ radical and $R_3$ denotes a hydrogen atom, i.e. 2-methyl-5-(3-methylidenecamphor)benzenesulphonic acid.

$R_2$ denotes a chlorine atom in the para position of the benzylidenecamphor, $R_4$ denotes an $—SO_3H$ radical and $R_3$ denotes a hydrogen atom, i.e. 2-chloro-5-(3-methylidenecamphor)benzenesulphonic acid.

$R_2$ denotes a methyl radical in the para position of the benzylidenecamphor, $R_4$ denotes a hydrogen atom and $R_3$ denotes an $—SO_3H$ radical, i.e. 3-(4-methyl) benzylidenecamphor-10-sulphonic acid.

Formula (III)

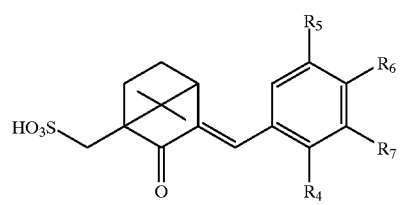

in which:

$R_5$ and $R_7$ denote a hydrogen atom, a hydroxyl radical, a linear or branched alkyl or alkoxy radical containing from 1 to 8 carbon atoms approximately, at least one of the radicals $R_5$ and $R_7$ representing a hydroxyl, alkyl or alkoxy radical, $R_6$ and $R_8$ denote a hydrogen atom or a hydroxyl radical, at least one of the radicals $R_6$ and $R_8$ denoting a hydroxyl radical, with the proviso that when $R_5$ and $R_8$ denote a hydrogen atom and $R_6$ denotes a hydroxyl radical, $R_7$ cannot denote an alkoxy radical or a hydrogen atom.

As specific examples, mention may be made of the following compounds of formula (III) in which:

$R_5$ is a methyl radical, $R_6$ is a hydrogen atom, $R_7$ is a tert-butyl radical and $R_8$ is a hydroxyl radical, i.e. (3-t-butyl-2-hydroxy-5-methyl)benzylidenecamphor-10-sulphonic acid.

$R_5$ is a methoxy radical, $R_6$ is a hydrogen atom, $R_7$ is a tert-butyl radical and $R_8$ is a hydroxyl radical, i.e. (3-t-butyl-2-hydroxy-5-methoxy)benzylidenecamphor-10-sulphonic acid.

$R_5$ and $R_7$ each denote a tert-butyl radical, $R_6$ denotes a hydroxyl radical and $R_8$ denotes a hydrogen atom, i.e. (3,5-di-tert-butyl-4-hydroxy)benzylidenecamphor-10-sulphonic acid.

Formula (IV)

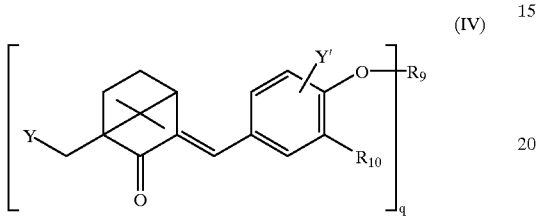

in which:

$R_9$ denotes a hydrogen atom, a linear or branched alkyl radical containing from 1 to 18 carbon atoms approximately or a linear or branched alkenyl radical containing from 3 to 18 carbon atoms approximately, a group

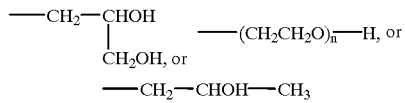

or alternatively a divalent radical: $-(CH_2)_m-$ or $-CH_2-CHOH-CH_2-$, n being an integer between 1 and 6 ($1 \leq n \leq 6$) and m being an integer between 1 and 10 ($1 \leq m \leq 10$), $R_{10}$ denotes a hydrogen atom, an alkoxy radical containing from 1 to 4 carbon atoms approximately or a divalent radical $-O-$ linked to the radical $R_9$ when the latter is also divalent, q denotes an integer equal to 1 or 2, it being understood that if q is equal to 2, $R_9$ must denote a divalent radical, Y and Y' denote a hydrogen atom or an $-SO_3H$ radical, at least one of these radicals Y or Y' being other than hydrogen.

As specific examples, mention may be made of the following compounds of formula (IV) in which:

q is equal to 1, Y and $R_{10}$ each denote a hydrogen atom, $R_9$ denotes a methyl radical and Y' in position 3 denotes an $-SO_3H$ radical, i.e. 2-methoxy-5-(3-methylidenecamphor)benzenesulphonic acid.

q is equal to 1, Y denotes an $-SO_3H$ radical, Y' denotes a hydrogen atom and $R_{10}$ denotes a divalent $-O-$ radical linked to $R_9$ denoting a methylene radical, i.e. 3-(4,5-methylenedioxy)benzylidenecamphor-10-sulphonic acid.

q is equal to 1, Y denotes an $-SO_3H$ radical, Y' and $R_{10}$ both denote a hydrogen atom and $R_9$ denotes a methyl radical, i.e. 3-(4-methoxy)benzylidenecamphor-10-sulphonic acid.

q is equal to 1, Y denotes an $-SO_3H$ radical, Y' denotes a hydrogen atom, $R_9$ denotes a methyl radical and $R_{10}$ denotes a methoxy radical, i.e. 3-(4,5-dimethoxy)benzylidenecamphor-10-sulphonic acid.

q is equal to 1, Y denotes an $-SO_3H$ radical, Y' and $R_{10}$ both denote a hydrogen atom and $R_9$ denotes an n-butyl radical, i.e. 3-(4-n-butoxy)benzylidenecamphor-10-sulphonic acid.

q is equal to 1, Y denotes an $-SO_3H$ radical, Y' denotes a hydrogen atom, $R_9$ denotes an n-butyl radical and $R_{10}$ denotes a methoxy radical i.e. 3-(4-n-butoxy-5-methoxy)benzylidenecamphor-10-sulphonic acid.

Formula (V)

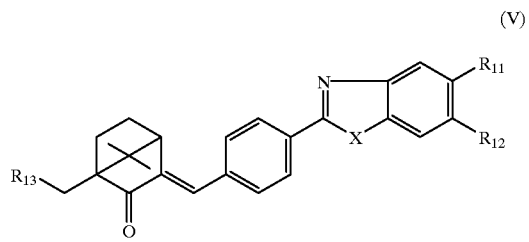

in which:

$R_{11}$ denotes a hydrogen atom, a linear or branched alkyl or alkoxy radical containing from 1 to 6 carbon atoms approximately or an $-SO_3H$ radical, $R_{12}$ denotes a hydrogen atom or a linear or branched alkyl or alkoxy radical containing from 1 to 6 carbon atoms approximately, $R_{13}$ denotes a hydrogen atom or an $-SO_3H$ radical, at least one of the radicals $R_{11}$ and $R_{13}$ denoting an $-SO_3H$ radical, X is an oxygen or sulphur atom or a group $-NR-$, R being a hydrogen atom or a linear or branched alkyl radical containing from 1 to 6 carbon atoms approximately.

As a specific example of formula (V), mention may be made of the compound in which X denotes an $-NH-$ radical, $R_{11}$ denotes an $-SO_3H$ radical and $R_{12}$ and $R_{13}$ both denote a hydrogen atom, i.e. 2-[4-(camphormethylidene)phenyl]benzimidazole-5-sulphonic acid.

The compounds of structures (I), (II), (III), (IV) and (V) above are described, respectively, in U.S. Pat. No. 4,585,597 and patent applications FR 2,236,515, 2,282,426, 2,645,148, 2,430,938 and 2,592,380.

The screening agent containing a sulphonic group can also be a sulphonic derivative of benzophenone of formula (VI) below:

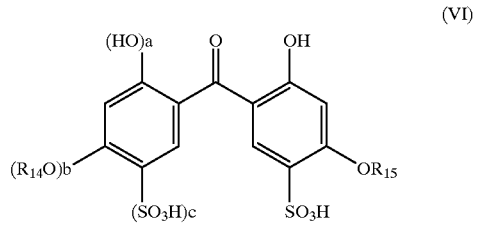

in which:

$R_{14}$ and $R_{15}$, which may be identical or different, denote either a hydrogen atom or a linear or branched alkyl radical containing from 1 to 8 carbon atoms approximately, a, b and c, which may be identical or different, are numbers equal to 0 or 1.

As a specific example of a compound of formula (VI), mention may be made of: 2-hydroxy-4-methoxybenzophenone-5-sulphonic acid (compound of formula (VI) in which a, b and c are equal to zero and $R_{15}$ denotes a methyl radical).

The screening agent containing a sulphonic group can also be a sulphonic derivative of formula (VII) below:

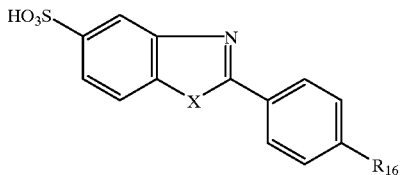

(VII)

in which:

X denotes an oxygen atom or an —NH— radical, $R_{16}$ denotes a hydrogen atom, a linear or branched alkyl or alkoxy radical containing from 1 to 8 carbon atoms approximately or a group of formula (VIII):

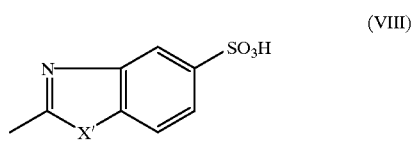

(VIII)

in which X' represents an oxygen atom or an —NH— radical.

As specific examples, mention may be made of the following compounds of formula (VII) in which:

X denotes an —NH— radical and $R_{16}$ denotes a hydrogen atom: 2-phenylbenzimidazole-5-sulphonic acid. This screening agent has excellent photoprotective power in the UV-B radiation range and is sold under the trade name "Eusolex 232" by the company Merck.

X denotes an —NH— radical and $R_{16}$ denotes a group of formula (VIII) in which X' denotes an —NH— radical: benzene-1,4-di(benzimidazol-2-yl-5-sulphonic acid).

X denotes an oxygen atom and $R_{16}$ denotes a group of formula (VIII) in which X' denotes an oxygen atom: benzene-1,4-di(benzoxazol-2-yl-5-sulphonic acid).

The compounds of formulae (VI) and (VII) are known compounds which can be prepared according to standard methods described in the prior art.

The hydrophilic screening agent(s) can be present in the final composition according to the invention in a content which can range from 0.1 to 20%, preferably from 0.2 to 10%, by weight relative to the total weight of the composition.

b) Lipophilic Screening Agents

As lipophilic screening agents which can be used in the invention, mention may be made advantageously of the family of screening agents derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607; 4-(tert-butyl)-4'-methoxydibenzoylmethane is moreover currently sold under the trade name "Parsol 1789" by the company Givaudan.

4-(tert-Butyl)-4'-methoxydibenzoylmethane has the following structural formula:

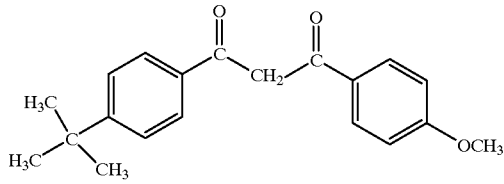

Another dibenzoylmethane derivative which is preferred according to the present invention is 4-isopropyldibenzoylmethane, this screening agent being sold under the name "Eusolex 8020" by the company Merck and corresponding to the following structural formula:

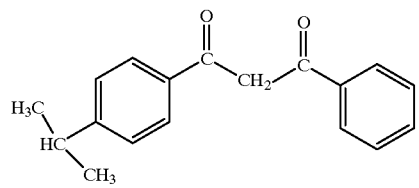

Similarly, 2-ethylhexyl α-cyano-β, β-diphenylacrylate, also known as octocrylene, is a liquid lipophilic screening agent that is already known for its activity in the UV-B range. This is a product which is commercially available, and is sold in particular under the name "Uvinul N 539" by the company BASF. It corresponds to the following formula:

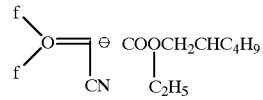

in which φ denotes a phenyl radical.

As another lipophilic (or liposoluble) screening agent which can be used in the invention, mention may also be made of p-methylbenzylidenecamphor, which is also known as a UV-B absorber and is sold in particular under the trade name "Eusolex 6300" by the company Merck.

The lipophilic screening agent(s) can be present in the composition according to the invention in a content which can range from 0.5 to 30%, preferably from 0.5 to 20%, of the total weight of the composition.

Other examples of lipophilic or hydrophilic organic screening agents are given in particular in patent application EP-A-0,487,404.

The compositions according to the invention can also contain agents for artificially tanning and/or browning the skin (self-tanning agents), such as, for example, dihydroxyacetone (DHA).

The cosmetic and/or dermatological compositions according to the invention can also contain pigments or alternatively nanopigments (average primary particle size: generally between 5 nm and 100 nm, preferably between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminium stearate, and silicones. Such coated or uncoated metal oxide nanopigments are described in particular in patent applications EP-A-0,518, 772 and EP-A-0,518,773.

The nanopigments can be present in the composition according to the invention in a content which can range from 0.1 to 20%, preferably from 0.2 to 10%, by weight relative to the total weight of the composition.

The fatty phase of the composition according to the invention can contain one or more oils (that are liquid at temperature) and optionally one or more waxes (that are solid at room temperature). These oils and waxes are those used conventionally in the fields concerned.

As oils which can be used in the invention, mention may be made in particular of:

- hydrocarbon-based oils of animal origin, such as perhydrosqualene;
- hydrocarbon-based plant oils, such as liquid fatty acid triglycerides, for example sunflower oil, corn oil, soybean oil, marrow oil, grapeseed oil, sesame oil, hazelnut oil, apricot oil, macadamia oil, castor oil or avocado oil, caprylic/capric acid triglycerides such as those sold by the company Stearineries Dubois or those sold under the names Miglyol 810, 812 and 818 by the company Dynamit Nobel;
- oils of formula $R_9COOR_{10}$ in which $R_9$ represents a higher fatty acid residue containing from 7 to 19 carbon atoms and $R_{10}$ represents a branched hydrocarbon-based chain containing from 3 to 20 carbon atoms, such as, for example, purcellin oil;
- linear or branched hydrocarbons of mineral or synthetic origin, such as non-volatile liquid paraffins and their derivatives, petroleum jelly, polydecenes and hydrogenated polyisobutene such as parleam;
- synthetic esters and ethers such as isopropyl myristate and octanoates, decanoates or ricinoleates of alcohols or of polyalcohols;
- fatty alcohols such as actyldodecanol or oleyl alcohol;
- partially hydrocarbon-based and/or silicone-based fluoro oils, such as that described in document JP-A-2-295, 912;
- silicone oils such as linear or cyclic polymethylsiloxanes which may or may not be volatile at room temperature and which may be liquid or pasty at room temperature, phenyldimethicones, phenyltrimethicones and polymethylphenylsiloxanes;
- mixtures thereof.

The oils represent from 1 to 50% of the total weight of the composition, preferably between 1 and 35%, and are chosen as a function of their comparability with the elastomeric organopolysiloxanes.

The waxes can be hydrocarbon-based, silicone and/or fluoro waxes.

The composition of the invention can also comprise any additive usually used in the field concerned, water-soluble or liposoluble dyes, antioxidants, essential oils, preserving agents, neutralizers, aqueous-phase or fatty-phase gelling agents, liposoluble polymers, cosmetic or dermatological active agents, such as, for example, emollients, moisturizers, vitamins, anti-wrinkle active agents and essential fatty acids. These additives can be present in the composition in a proportion of from 0 to 20% of the total weight of the composition, and better still from 0 to 10%.

Needless to say, a person skilled in the art will take care to select the optional complementary additives and/or the amount thereof such that the advantageous properties of the composition according to the invention are not, or are not substantially, adversely affected by the addition envisaged.

The composition can be in coloured or uncoloured form depending on whether it constitutes a care product or a make-up product.

Needless to say, the composition of the invention must be cosmetically or dermatologically acceptable, i.e it must be non-toxic and capable of being applied to human skin or lips.

The composition of the invention can comprise a particulate phase, which is generally present in a proportion of from 0 to 35% of the total weight of the composition, preferably from 5 to 25%, and which can comprise pigments and/or pearlescent agents and/or fillers, which are coloured and which are usually used in cosmetic compositions.

The composition according to the invention can be manufactured by known processes generally used in the cosmetics or dermatological field.

The subject of the invention is also a cosmetic process to care for or treat human skin or lips, comprising the application of the composition as defined above to the skin or the lips.

The invention is illustrated in greater detail in the examples which follow. The percentages are given by weight.

EXAMPLE 1

Antisun Cream

| | |
|---|---|
| Glycerol | 6 |
| Triethanolamine | 2.36 |
| Demineralized water qs | 100 |
| Preserving agents | 1.2 |
| Palm oil stearic acid | 2 |
| Arlacel 165 (iron: ICI) | 1 |
| Stearyl heptanoate/caprylate (67/30) | 2 |
| $C_{12}/C_{15}$ Alkyl benzoate | 9 |
| 4-tert-Butyl-4'-methoxydibenzoylmethane | 4 |
| Vinylpyrrolidone/eicosene copolymer | 1 |
| Potassium hexadecyl phosphate | 1 |
| 2,2,4,4,6,6,8-Heptamethylnonane | 3 |
| Rutile titanium oxide (15 nm) treated with aluminium stearate/albumin | 5 |
| B-B' Camphorsulphonic [1-4-divinylbenzene] acid as an aqueous 33% solution | 9 |
| 2-Ethylhexyl 2-cyano-3,3-diphenylacrylate | 10 |
| Polydimethylsiloxane/crosslinked polydimethylsiloxane mixture (76/24) (KSG-16) | 2.5 |

This milk is a soft oil-in-water fluid emulsion which feels pleasant and is not sticky or shiny on the skin. having water-remanent screening properties and a very high UV protection factor of 105.

EXAMPLE 2

Antisun Milk

| | |
|---|---|
| Glycerol | 4 |
| Triethanolamine | 1.07 |
| Demineralized water qs | 100 |
| Preserving agents | 1 |
| Palm oil stearic acid | 2.2 |
| Arlacel 165 (iron: ICI) | 1 |
| Stearyl heptanoate/caprylate (67/30) | 4 |
| Crosslinked polydimethylsiloxane/ Polymethylphenylsiloxane mixture (60/40) | 2.5 |

-continued

| | |
|---|---|
| 4-tert-Butyl-4'-methoxydibenzoylmethane | 2 |
| Silicone (Dow Corning 3225 C (iron: Dow Corning)) | 1 |
| alpha-omega-Dihydroxyl polydimethylsiloxane/ cyclotetra- and cyclopentadimethylsiloxane mixure (56/44) | 2.5 |
| Potassium hexadecyl phosphate | 1 |
| 2,2,4,4,6,6,8-Heptamethylnonane | 3 |
| Rutile titanium oxide (15 nm) treated with aluminium stearate/albumin | 5 |
| B-B' Camphorsulphonic [1-4-divinylbenzene[ acid as an aqueous 33% solution | 3 |
| Cyclohexadimethylsiloxane | 5 |
| 2-Ethylhexyl 2-cyano-3,3-diphenylacrylate | 10 |

This milk of oil-in-water type is non-greasy and non-sticky. It has a high protection factor (SPF of 25) and excellent remanence to water.

EXAMPLE 3
Antisun Cream

| | |
|---|---|
| Silicone (DC 5200 formulation Aid Dow Corning) | 2 |
| Oxyethylene and oxypropylene polymethyllauryl/ methylsiloxane Arlacel P 135 (ICI) | 2 |
| Polyethylene glycol di-polyhydroxystearate (30 DE) | |
| Finsolv TN (stearinerie Dubois) | 6 |
| $C_{12}/C_{15}$ alkyl benzoate | 10 |
| Silicone (DC 246 Fluid (Dow Corning) cyclohexadimethylsiloxane) | |
| Preserving agent | qs |
| $TiO_2$ T 805 (Degussa) | 3 |
| Uvinul N539 | 4 |
| Eusolex 6300 | 4 |
| Parsol 1789 | 2 |
| NaCl | 1 |
| Glycerol | 4 |
| Sequestering agent | 0.3 |
| Mexoryl SX | 0.5 AM |
| Triethanolamine | 0.26 |
| KSG 16 | 4 |
| Purified water   qs | 100 |

This cream of water-in-oil type is not sticky and not shiny after it has been applied to the skin. Its protection factor is 35 and it is water-resistant. Comparative sensory analysis of 2 formulations of water-in-oil type, one containing 4% KSG-16, the other not containing any; the results are given in the table below, cosmetic evaluation is graded from 0 to 5 (from poor to good). These compositions correspond to that of Example 3 with or without KSG-16.

From this table it emerges clearly that the introduction of elastomeric organopolysiloxane makes it possible to increase the cosmetic properties of the compositions and in particular the non-greasy, non-sticky appearance and the softness.

Moreover, the composition of Example 1 with KSG has a protection factor of 105, whereas this same composition without KSG only has a protection factor of 80.3. Thus, in addition to the enhancement of the cosmetic properties of the compositions, the organopolysiloxanes according to the invention appreciably increase the protection factor in the UV range.

The same types of results, i.e. enhancement of the cosmetic properties, are obtained with the milk of Example 2. Moreover, an increase in the protection factor (SPF) from 21.4 to 25.7 is observed.

I claim:

1. Composition comprising an aqueous phase containing at least one water-soluble sunscreen agent, a fatty phase containing at least one liposoluble sunscreen agent and at least one partially crosslinked, elastomeric, solid organopolysiloxane as a gelling agent.

2. Composition according to claim 1, wherein the elastomeric organopolysiloxane is obtained by addition reaction and crosslinking, in the presence of a catalyst, of at least:
   (a) an organopolysiloxane having at least two lower alkenyl groups per molecule; and/or
   (b) an organopolysiloxane having at least two hydrogen atoms linked to one silicon atom per molecule.

3. Composition according to claim 1, wherein the organopolysiloxane is chosen from:
   i) organopolysiloxanes comprising units $R_2SiO$ and $RSiO_{1.5}$ and optionally units $R_3SiO_{0.5}$ and/or $SiO_2$ wherein the radicals R, independently of each other, represent a hydrogen, an alkyl, an aryl, an unsaturated aliphatic group, the weight ratio of the units $R_2SiO$ to the units $RSiO_{1.5}$ ranging from 1/1 to 30/1;
   ii) organopolysiloxanes which are insoluble in silicone oil, obtained by addition of an organohydrogenopolysiloxane (1) and an organopolysiloxane (2) having unsaturated aliphatic groups such that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic.

4. Composition according to claim 1, wherein the fatty phase contains one or more oils chosen from hydrocarbon-based oils, silicone oils and/or fluoro oils.

5. Composition according to, claim 1, wherein the fatty phase represents 1 to 50% of the total weight of the composition.

| | Control No. 1 | | Control No. 2 | | Control No. 3 | | Control No. 4 | | Control No. 5 | | Average | |
|---|---|---|---|---|---|---|---|---|---|---|---|---|
| | without | 4% KSG-16 | without | 4% KSG-16 | without | 4% KSG-16 | without | 4% KSG 16 | without | 4% KSG 16 | without | 4% KSG 16 |
| Abs shiny | 2 | 4 | 2 | 4 | 3 | 5 | 2 | 5 | 2 | 4 | 2.20 | 4.40 |
| Abs greasy | 3.5 | 3 | 3.5 | 3 | 2 | 3.5 | 3 | 5 | 2 | 4 | 2.80 | 3.70 |
| Abs sticky | 2.5 | 2.5 | 3 | 3 | 2 | 4 | 4 | 5 | 3 | 4 | 2.90 | 3.70 |
| Softness | 1 | 4 | 2 | 3 | 1 | 4 | 2 | 5 | 3 | 3 | 1.80 | 3.80 |

6. Composition according to, claim 1 wherein the hydrophilic sunscreen agent(s) represent(s) from 0.1 to 20% of the total weight of the composition.

7. Composition according to claim 1, wherein the lipophilic sunscreen agent(s) is (are) present from 0.5 to 30% of the total weight of the composition.

8. Composition according to claim 1, wherein the composition further comprises metal oxide nanopigments.

9. Composition according to claim 1, wherein the nanopigments represent from 0.1 to 20% of the total weight of the composition.

10. Composition according to claim 1, wherein the hydrophilic sunscreen agent(s) comprise(s) sulphonic derivatives of 3-benzylidene-2-camphor, sulphonic derivatives of benzophenone, sulphonic derivatives of benzimidazole, p-aminobenzoic acid derivatives and benzene-1,4-di (benzoxazol-2-yl-5-sulphonic acid), and mixtures thereof.

11. Composition according to claim 1, wherein the lipophilic screening agent(s) comprise(s) dibenzoylmethane derivatives, β,β-diphenylacrylate derivatives, triazine derivatives, p-methylbenzylidenecamphor, screening polymers, screening silicones and salicyclic derivatives, and mixtures thereof.

12. Composition according to claim 1, further comprises fillers and/or pigments and/or pearlescent agents.

13. Composition according to claim 1, wherein the composition further comprises at least one additive comprising antioxidants, essential oils, preserving agents, neutralizers, fatty-phase or aqueous-phase gelling agents, electrolytes, liposoluble polymers and cosmetic or dermatological active agents.

14. Composition according to claim 1, wherein the active agents comprise emollients, moisturizers, vitamins, anti-wrinkle active agents and essential fatty acids.

15. Composition according to claim 1, wherein the composition constitutes a care composition, a treatment composition and/or a make-up composition.

16. Process for protecting the skin and/or the lips against solar radiation, comprising applying an effective amount of the composition according to claim 1 to the skin and/or the lips of a human or animal.

* * * * *